United States Patent
Tsuta (10) Patent No.: US 8,550,630 B2
(45) Date of Patent: Oct. 8, 2013

(54) MACULAR REGION VISUAL DEFECT INDEX CALCULATION APPARATUS

(75) Inventor: Tomohiro Tsuta, Kobe (JP)

(73) Assignee: Tomohiro Tsuta, Kobe (JP)

( * ) Notice: Subject to any disclaimer, the term of this patent is extended or adjusted under 35 U.S.C. 154(b) by 185 days.

(21) Appl. No.: 12/998,053

(22) PCT Filed: Aug. 25, 2009

(86) PCT No.: PCT/JP2009/064797
§ 371 (c)(1),
(2), (4) Date: Jun. 20, 2011

(87) PCT Pub. No.: WO2010/032590
PCT Pub. Date: Mar. 25, 2010

(65) Prior Publication Data
US 2011/0267585 A1    Nov. 3, 2011

(30) Foreign Application Priority Data
Sep. 16, 2008    (JP) .................................. 2008-325929

(51) Int. Cl.
*A61B 3/02* (2006.01)
*A61B 3/00* (2006.01)
(52) U.S. Cl.
USPC ......................................... 351/224; 351/246
(58) Field of Classification Search
USPC ................................................ 351/224, 246
See application file for complete search history.

(56) References Cited

FOREIGN PATENT DOCUMENTS

| JP | S58-121937 | 7/1983 |
| JP | H4-135534 | 5/1992 |
| JP | H12-262471 | 9/2000 |
| JP | H14-306413 | 10/2002 |
| JP | H15-199711 | 7/2003 |
| JP | H16-73545 | 3/2004 |
| JP | H19-29112 | 2/2007 |
| JP | H19-75350 | 3/2007 |
| JP | H20-36297 | 2/2008 |
| WO | WO2006/106877 | 10/2006 |

*Primary Examiner* — Jack Dinh (57) ABSTRACT

A macular region visual defect index calculation apparatus including: visual field probe screen generating means; fixation image displaying and controlling means; probe region setting means; probe points setting means; visual target displaying and controlling means; first counting means; second detection means; second counting means; and visual defect index calculation means for dividing the number of times counted and stored on a memory device by the second counting means, by the total number counted and stored on a memory device by the first counting means; wherein the probe region being locally set mainly in macular region. So, according to the present invention of a macular region visual defect index calculation apparatus, a ratio of visual defect region to macular region can be calculated as an index, and the degree of visual defect against macular region can be numerically grasped.

4 Claims, 6 Drawing Sheets

MACULAR REGION VISUAL DEFECT INDEX CALCULATION APPARATUS

BACKGROUND OF THE INVENTION

The present invention relates to a macular region visual defect index calculation apparatus, a method for a macular region visual defect index calculation apparatus, a program for realizing a macular region visual defect index calculation apparatus, and a non-transitory computer-readable recorded medium.

Previous perimeters include: Goldmann perimeter model 510 [1945] and model 940 [1967]; Tubinger perimeter [1957]; and Octopus perimeter [1976].

(See, e.g., the non-patent literature 1.)

The previous perimeters are explained:

Goldmann perimeter is the first brightness perimeter, adopting the method of simultaneous manual recording, with 4 to 60 degrees of brightness of the visual target and 6 types of visual angle of the visual target, capable of examining visual field of visual angle, and with adjustability of its background brightness. The shortcoming is that it fails to examine the central region within 5 degrees;

Tubinger perimeter [1957] is the first practical static perimeter, capable of examining the kinetic visual field and the visual field of color, flicker, and etc., adopting the method of simultaneous manual recording, with 80 degrees of brightness of the visual target and 100 degrees of brightness of the fixation image and 5 kinds of color and 6 degrees of background brightness, and capable of examining the central and eccentric vision. Its shortcoming is in the difficulty of controlling the visual target movement, and of adjusting the visual target, fixation image, and background illumination lamp;

Octopus perimeter [1976] is the world's first fully automated static perimeter.

Non-patent literature 1: "The latest comprehensive dictionary of medical science", Ishiyaku Publishers Inc., 1987, 1990.

Previous perimeters don't calculate the ratio of visual defect area to macular region. The degree of visual defect against macular region of a subject is not evaluated numerically by previous perimeters.

The aim of the present invention is, therefore, to provide a macular region visual defect index calculation apparatus which allows for calculation of the ratio of visual defect area to macular region.

SUMMARY OF THE INVENTION

To achieve the above aim, the invention of claim 1 is a macular region visual defect index calculation apparatus including:

means for generating, on an output device, a visual field probe screen for probing a visual field of a subject using a static visual target;

means for displaying and controlling a fixation image to be fixated by the subject during a visual field probe, on the visual field probe screen generated by said visual field probe screen generating means;

means for setting a circular region surrounding the fixation image displayed by said fixation image displaying and controlling means, as a probe region in order to probe the subject's visual field using the static visual target;

means for setting a plurality of probe points, with equal spacing, in the probe region set by said probe region setting means;

means for displaying and controlling the static visual target sequentially on the probe points set by said probe points setting means to probe the visual field corresponding to the probe points;

first counting means for counting, and storing on a memory device, a total number of said probe points at which the static visual target has been displayed by said visual target displaying and controlling means;

second detection means for detecting that the static visual target, displayed by said visual target displaying and controlling means, has not been perceived;

second counting means for counting via an arithmetic unit and storing on a memory device, the number of times of detecting, through said second detection means, that said static visual target has not been visually perceived;

and means for calculating a visual defect index, via an arithmetic unit, by dividing said number of times counted and stored on the memory device by said second counting means, by said total number counted and stored on the memory device by said first counting means;

wherein said probe region being set locally from a viewpoint of probing visual field characteristics mainly in macular region, and said visual defect index being a visual defect index from a viewpoint of probing visual field characteristics mainly in macular region.

The invention of claim 2 is a program for causing a computer to realize the function including:

means for generating, on an output device, a visual field probe screen for probing a visual field of a subject using a static visual target;

means for displaying and controlling a fixation image to be fixated by the subject during a visual field probe, on the visual field probe screen generated by said visual field probe screen generating means;

means for setting a circular region surrounding the fixation image displayed by said fixation image displaying and controlling means, as a probe region in order to probe the subject's visual field using the static visual target;

means for setting a plurality of probe points, with equal spacing, in the probe region set by said probe region setting means;

means for displaying and controlling the static visual target sequentially on the probe points set by said probe points setting means to probe the visual field corresponding to the probe points;

first counting means for counting, and storing on a memory device, a total number of said probe points at which the static visual target has been displayed by said visual target displaying and controlling means;

second detection means for detecting that the static visual target, displayed by said visual target displaying and controlling means, has not been perceived;

second counting means for counting via an arithmetic unit and storing on a memory device, the number of times of detecting, through said second detection means, that said static visual target has not been visually perceived;

and means for calculating a visual defect index, via an arithmetic unit, by dividing said number of times counted and stored on the memory device by said second counting means, by said total number counted and stored on the memory device by said first counting means;

wherein said probe region being set locally from a viewpoint of probing visual field characteristics mainly in macular region, and said visual defect index being a visual defect index from a viewpoint of probing visual field characteristics mainly in macular region.

The invention of claim 3 is an operational method for a macular region visual defect index calculation apparatus including:

a step of means for generating, on an output device, a visual field probe screen for probing a visual field of a subject using a static visual target;

a step of means for displaying and controlling a fixation image to be fixated by the subject during a visual field probe, on the visual field probe screen generated by said step of visual field probe screen generating means;

a step of means for setting a circular region surrounding the fixation image displayed by said step of fixation image displaying and controlling means, as a probe region in order to probe the subject's visual field using the static visual target;

a step of means for setting a plurality of probe points, with equal spacing, in the probe region set by said step of probe region setting means;

a step of means for displaying and controlling the static visual target sequentially on the probe points set by said step of probe points setting means to probe the visual field corresponding to the probe points;

a step of first counting means for counting, and storing on a memory device, a total number of said probe points at which the static visual target has been displayed by said step of visual target displaying and controlling means;

a step of second detection means for detecting that the static visual target, displayed by said step of visual target displaying and controlling means, has not been perceived;

a step of second counting means for counting via an arithmetic unit and storing on a memory device, the number of times of detecting, through said step of second detection means, that said static visual target has not been visually perceived;

and a step of means for calculating a visual defect index, via an arithmetic unit, by dividing said number of times counted and stored on the memory device by said step of second counting means, by said total number counted and stored on the memory device by said step of first counting means;

wherein said probe region being set locally from a viewpoint of probing visual field characteristics mainly in macular region, and said visual defect index being a visual defect index from a viewpoint of probing visual field characteristics mainly in macular region.

The invention of claim 4 is a non-transitory computer-readable recorded medium recording a program for causing a computer to realize the function including:

means for generating, on an output device, a visual field probe screen for probing a visual field of a subject using a static visual target;

means for displaying and controlling a fixation image to be fixated by the subject during a visual field probe, on the visual field probe screen generated by said visual field probe screen generating means;

means for setting a circular region surrounding the fixation image displayed by said fixation image displaying and controlling means, as a probe region in order to probe the subject's visual field using the static visual target;

means for setting a plurality of probe points, with equal spacing, in the probe region set by said probe region setting means;

means for displaying and controlling the static visual target sequentially on the probe points set by said probe points setting means to probe the visual field corresponding to the probe points;

first counting means for counting, and storing on a memory device, a total number of said probe points at which the static visual target has been displayed by said visual target displaying and controlling means;

second detection means for detecting that the static visual target, displayed by said visual target displaying and controlling means, has not been perceived;

second counting means for counting via an arithmetic unit and storing on a memory device, the number of times of detecting, through said second detection means, that said static visual target has not been visually perceived;

and means for calculating a visual defect index, via an arithmetic unit, by dividing said number of times counted and stored on the memory device by said second counting means, by said total number counted and stored on the memory device by said first counting means;

wherein said probe region being set locally from a viewpoint of probing visual field characteristics mainly in macular region, and said visual defect index being a visual defect index from a viewpoint of probing visual field characteristics mainly in macular region.

So, according to the first invention of a macular region visual defect index calculation apparatus, a ratio of visual defect region to macular region can be calculated as an index of visual defect.

And, according to the first invention of a macular region visual defect index calculation apparatus, the degree of visual defect against macular region can be numerically grasped.

So, according to the second invention of a program, a macular region visual defect index calculation apparatus can be realized by carrying out the program, and a ratio of visual defect region to macular region can be calculated as an index of visual defect.

And, according to the second invention of a program, the degree of visual defect against macular region can be numerically grasped.

So, according to the third invention of an operational method for a macular region visual defect index calculation apparatus, a ratio of visual defect region to macular region can be calculated as an index of visual defect.

And, according to the third invention of an operational method for a macular region visual defect index calculation apparatus, the degree of visual defect against macular region can be numerically grasped.

So, according to the fourth invention of a non-transitory computer-readable recorded medium which records a program, it becomes possible to make a program to realize a macular region visual defect index calculation apparatus computer-readable, and a macular region visual defect index calculation apparatus can be realized by carrying out the program to realize a macular region visual defect index calculation apparatus, and a ratio of visual defect region to macular region can be calculated as an index of visual defect.

Also the degree of visual defect against macular region can be numerically grasped.

The macular region visual defect index calculation apparatus of the present invention may be embodied by a simple setup without the need for voluminous equipment such as Goldmann perimeter or the like.

The macular region visual defect index calculation apparatus of the present invention can examine the central portion within 5 degrees of the visual field.

DETAILED DESCRIPTION OF THE INVENTION

The detailed explanation of the present invention of a macular region visual defect index calculation apparatus, a method for a macular region visual defect index calculation apparatus, a program for realizing a macular region visual defect index calculation apparatus, and a non-transitory computer-readable recorded medium will be disclosed as below while referring to the drawings.

Figure 1:
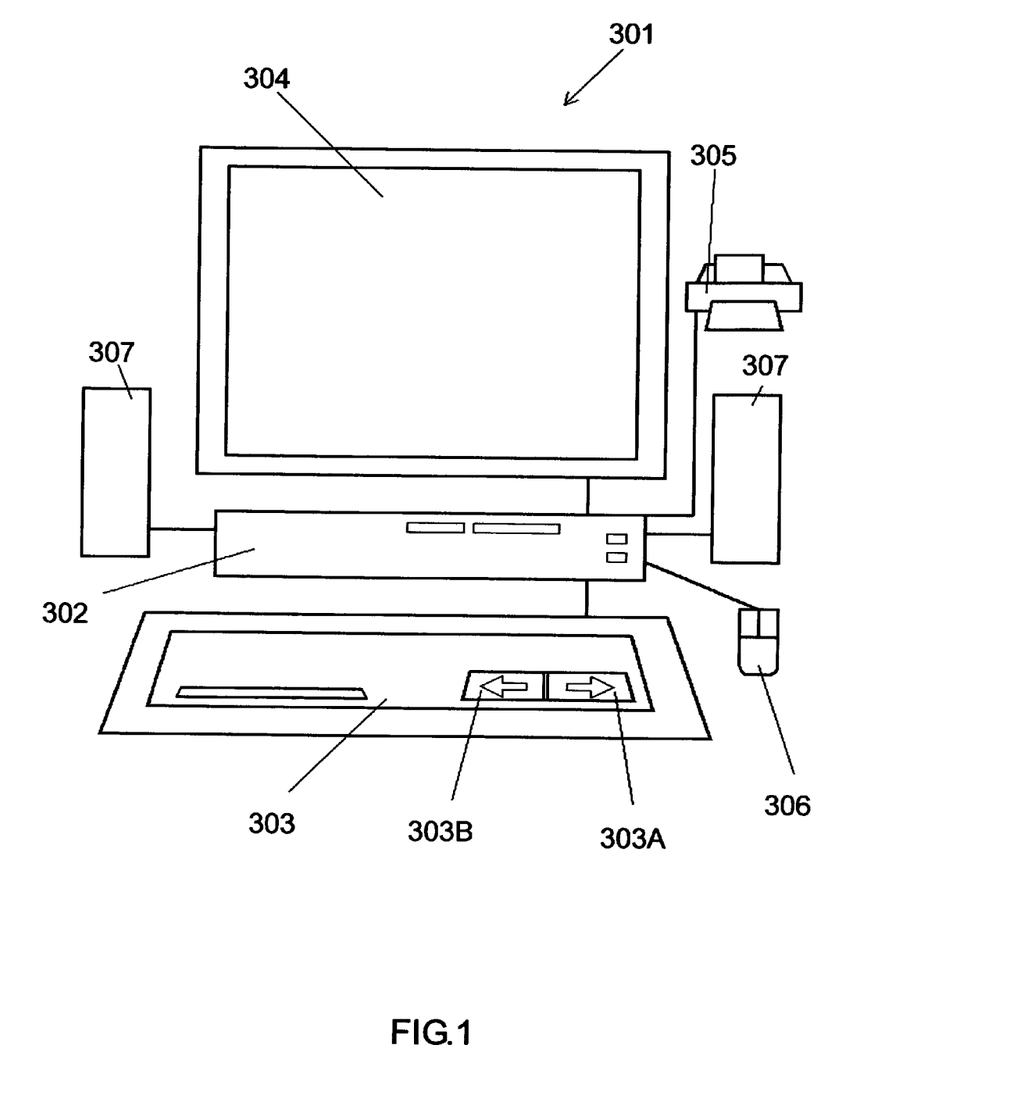
FIG. 1 is a diagram showing a preferred embodiment of the system of the present invention of a macular region visual defect index calculation apparatus.
Figure 2:
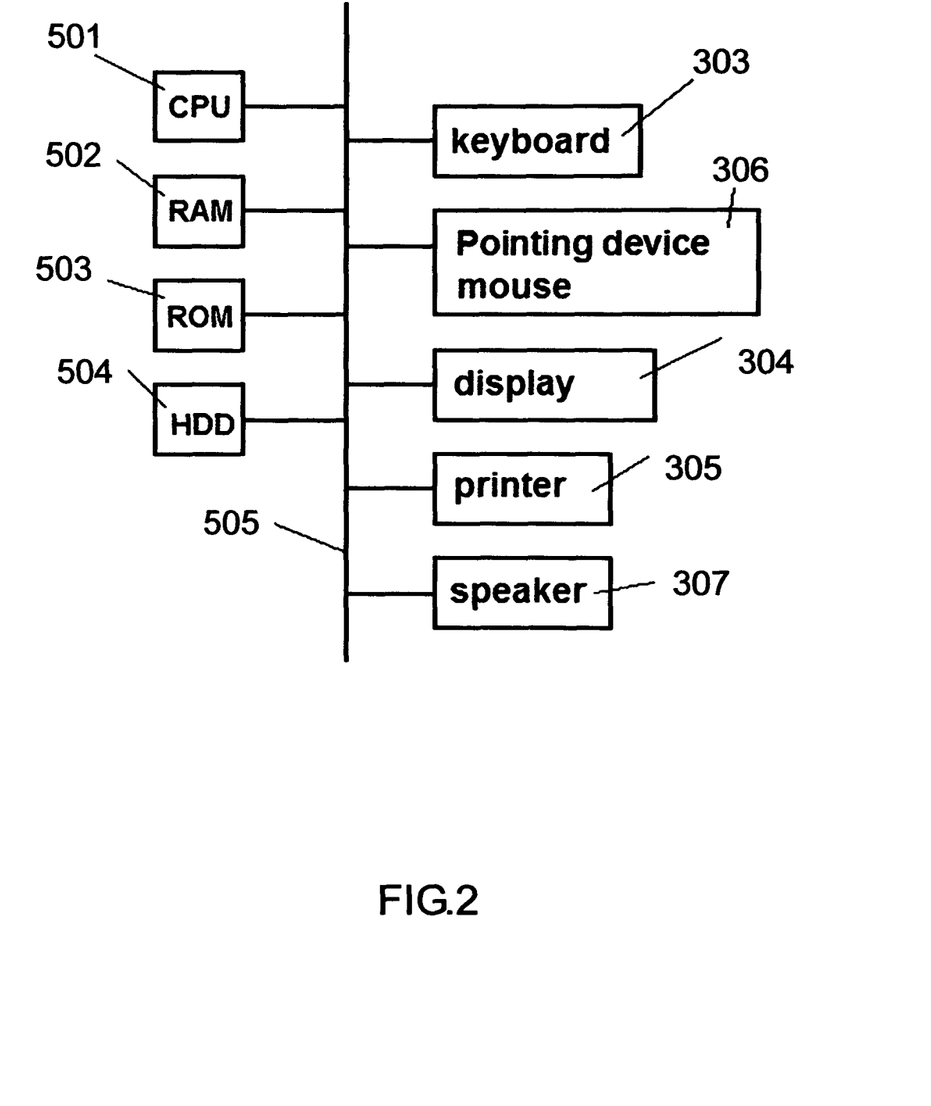
FIG. 2 is a block diagram showing a preferred embodiment of the hardware configuration of a CPU in the present invention of a macular region visual defect index calculation apparatus.

Firstly, a setup of the present invention of the static perimeter is described referring to FIG. 1 and FIG. 2.

FIG. 1 shows an embodiment of the system of the present invention of a macular region visual defect index calculation apparatus.

FIG. 2 shows an embodiment of the hardware configuration of a CPU 501 in the present invention of a macular region visual defect index calculation apparatus.

FIG. 1 shows a computer system 301 diagrammatically.

The present invention of a macular region visual defect index calculation apparatus is realized by the computer system 301 carrying out a program for realizing the macular region visual defect index calculation apparatus.

As shown in FIG. 1, the computer system 301 realizing an embodiment of the present invention of a macular region visual defect index calculation apparatus includes a main unit 302 that is equipped with a CPU (Central Processing Unit) 501, etc., which will be mentioned later, a keyboard 303, (if necessary, a mouse 306), a display 304, and a printer 305 (and if necessary, a speaker 307 too).

Next, an embodiment of the hardware configuration of the CPU 501 in the present invention of a macular region visual defect index calculation apparatus is described referring to FIG. 2.

The CPU 501 in the present invention of a macular region visual defect index calculation apparatus is configured specifically including:
a microprocessor such as the CPU 501, a RAM (Random Access Memory) 502, a ROM (Read Only Memory) 503, a HDD (Hard Disc Drive) 504, a keyboard 303, (a mouse 306,) a display 304, (a printer 305,) (a speaker 307,) (and a communications interface).
These parts are connected via a bus 505.
(The HDD 504 is connected through the input-output interface to the bus 505.)

The keyboard 303 is connected through the input-output interface to the bus 505, which enables output to the CPU 501 of input by the keyboard 303.

The display 304 is connected through the input-output interface to the bus 505, which enables output to the display 304 of image data input from the CPU 501.

The printer 305 is connected through the input-output interface to the bus 505, which enables output by the printer 305 of input from the CPU 501.

(The speaker 307 is connected through the input-output interface to the bus 505, which enables output by the speaker 307 of input from the CPU 501.)

(The mouse 306 is connected through the input-output interface to the bus 505, which enables output to the CPU 501 of input through the mouse 306.)

The CPU 501 carries out operations characteristic of an embodiment of the present invention, by loading onto the RAM 502 a program, which is stored in the HDD (Hard Disc Drive) 504, for realizing the present invention of a macular region visual defect index calculation apparatus.

The CPU 501 carries out controls, and kinds of arithmetic processing, of the present invention of a macular region visual defect index calculation apparatus, according to a program for realizing the present invention of a macular region visual defect index calculation apparatus.

The CPU 501 controls display processing of the display 304 (an example of the output device). (Specifically, the CPU 501, for example, displaying and controlling a fixation image and a static visual target, and generating a visual field mapping image from a data obtained by the present invention of a macular region visual defect index calculation apparatus.)

The CPU 501 controls the present invention of a macular region visual defect index calculation apparatus according to input by the keyboard 303 (an example of the input device).

The CPU 501 can control the printer 305 and the like so as to output the data obtained from a macular region visual defect index calculation apparatus.

(If necessary,
the CPU 501 may control the speaker 307 (an example of the output device) to produce output (for example, according to input by an input device such as the keyboard 303 or the like, or, for example, when a probe point is changed during a static visual field probe, or, for example, when a macular region visual defect index is calculated (output), or, for example, when the visual field mapping image is output, or the like).)

(The CPU 501 may control the present invention of a macular region visual defect index calculation apparatus according to input from the mouse 306 (an example of the input device).)

The keyboard 303 (and if necessary, the mouse 306) and the display 304 are used as user interfaces in the present invention of a macular region visual defect index calculation apparatus.

The keyboard 303 is used, for example, as a device for input (the input device).

(If necessary, the mouse 306 is used as a device for performing various kinds of operations of input to the display screen of the display 304.)

The display 304 is a display device (the output device), for example, of a LCD (Liquid Crystal Display), a CRT (Cathode Ray Tube), or the like, which probes a visual field in accordance with the present invention of a macular region visual defect index calculation apparatus, displays a macular region visual defect index calculated by the present invention of a macular region visual defect index calculation apparatus, and displays a visual field mapping image generated by the present invention of a macular region visual defect index calculation apparatus.

(If necessary, various screens such as an operation screen and a setting screen may be displayed on the display 304.)

And when the CPU 501 is connected to communications network such as the Internet and a LAN (Local Area Network), the communications interface can be equipped with a network adapter such as a LAN card or communications equipment such as a modem, in order to establish data communication among the network. In such a case, by installing on the network a server storing a program for realizing the present invention of a macular region visual defect index calculation apparatus, and configuring the CPU 501 as a client terminal of the server, the operation of the present invention of a macular region visual defect index calculation apparatus can be carried out by a macular region visual defect index calculation apparatus.

A program for realizing the present invention of a macular region visual defect index calculation apparatus can be stored on any non-transitory computer-readable recording media (storage media).

Examples of such non-transitory recording media (storage media) include an optical disk, a magneto-optic disk (CD-ROM, DVD-RAM, DVD-ROM, MO, etc.), a magnetic-storage device (hard disk, Floppy Disk™, ZIP, etc.), a semiconductor memory, etc.

Next, the detailed explanation regarding the present invention of a macular region visual defect index calculation apparatus, a method for a macular region visual defect index calculation apparatus, a program for realizing a macular region visual defect index calculation apparatus, and a non-transitory computer-readable recorded medium will be described while referring to FIG. 3, FIG. 4, FIG. 5, and FIG. 6, as below.

Figure 3:
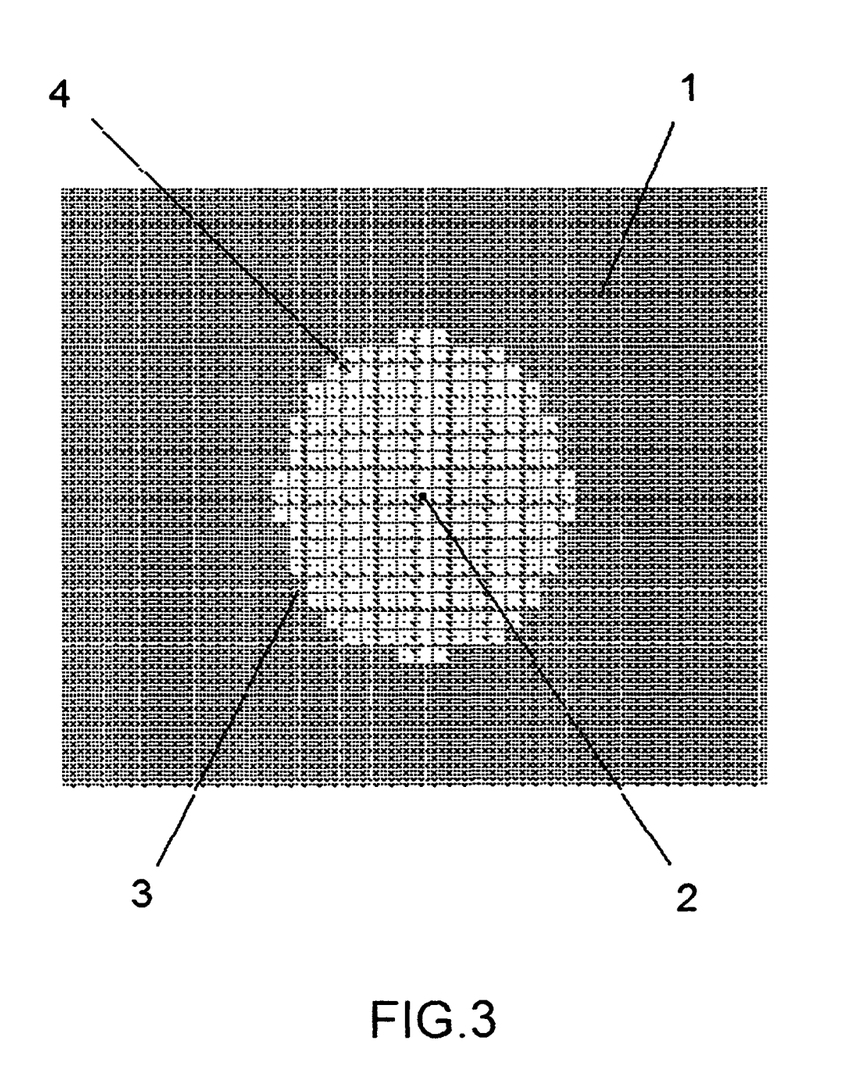
FIG. 3 is a schematic diagram showing a preferred embodiment of the probe and operational aspect of the present invention of a macular region visual defect index calculation apparatus.

FIG. 3 shows a schematic diagram of a preferred embodiment of the probe and operational aspect of the present invention of a macular region visual defect index calculation apparatus.

Figure 4:
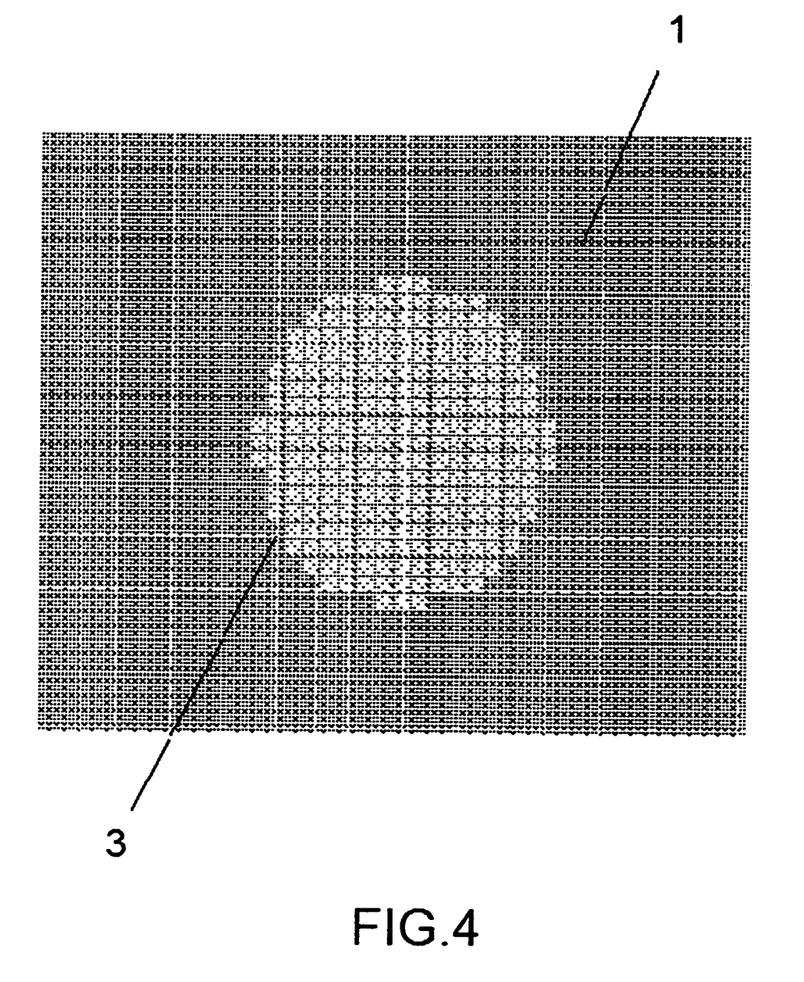
FIG. 4 is a schematic diagram showing a preferred embodiment of the macular region visual defect index calculation aspect of the present invention of a macular region visual defect index calculation apparatus.
Figure 5:
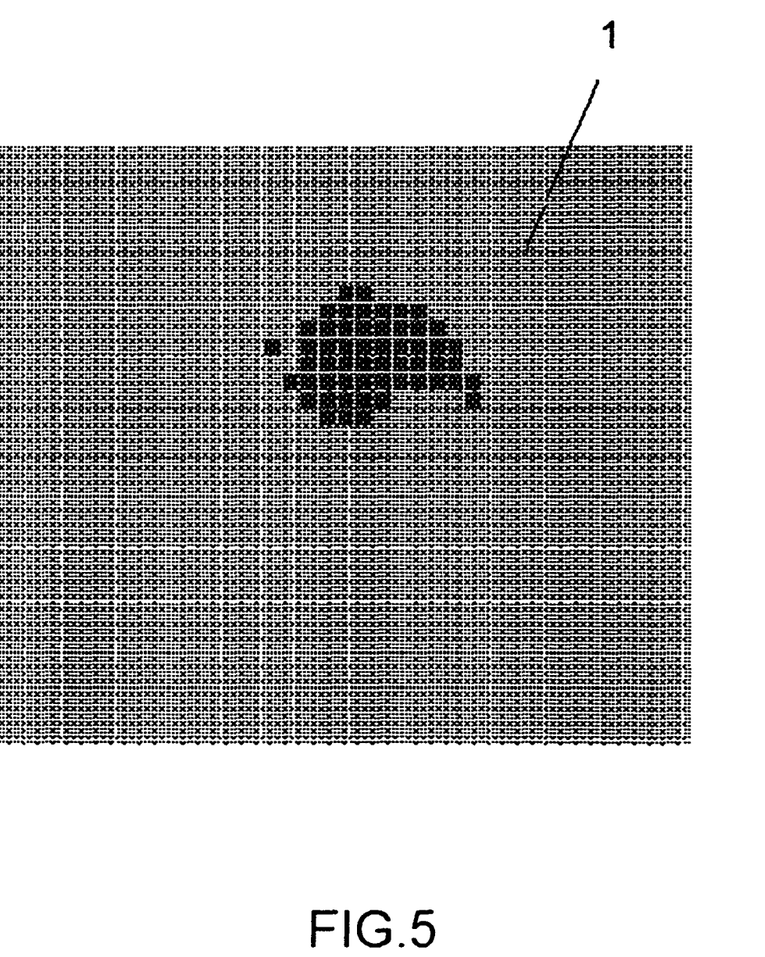
FIG. 5 is a schematic diagram showing a preferred embodiment of the macular region visual defect index calculation aspect of the present invention of a macular region visual defect index calculation apparatus.

FIG. 4 and FIG. 5 show schematic diagrams of a preferred embodiment of the macular region visual defect index calculation aspect of the present invention of a macular region visual defect index calculation apparatus.

Figure 6:
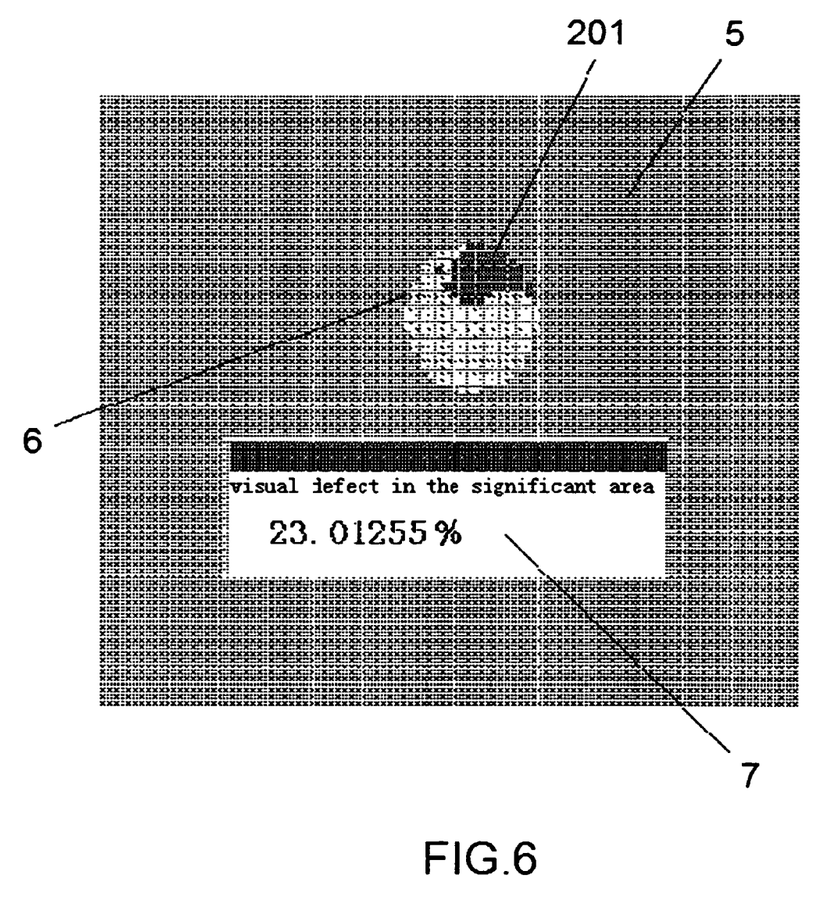
FIG. 6 is a schematic diagram showing a preferred embodiment of the macular region visual defect index calculation and visual field mapping image generating aspect and display screen aspect of the present invention of a macular region visual defect index calculation apparatus.

FIG. 6 shows a schematic diagram of a preferred embodiment of the macular region visual defect index calculation and visual field mapping image generating aspect and display screen aspect of the present invention of a macular region visual defect index calculation apparatus.

A CPU 501 generates, on an output device (for example, a display 304), a visual field probe screen 1 for probing a visual field of a subject using a static visual target.
(A visual field probe screen generating means.)

The CPU 501 displays a fixation image 2 to be fixated by (for example, an eye of) the subject during a visual field probe, on the visual field probe screen 1 generated by said visual field probe screen generating means, in accordance with a program for realizing the present invention of a macular region visual defect index calculation apparatus.
(A fixation image displaying and controlling means.)

The CPU 501 sets a circular region surrounding the fixation image 2 as a probe region 3 in order to probe the subject's visual field using the static visual target, in accordance with a program for realizing the present invention of a macular region visual defect index calculation apparatus.
(A probe region setting means.)
(A circular region may not be limited to a circle region. A circular region, for example, may be a region with elliptical shape.)

The CPU 501 sets (confines) a probe region 3 locally from a viewpoint of probing visual field characteristics mainly in macular region, in accordance with a program for realizing the present invention of a macular region visual defect index calculation apparatus.
(The CPU 501 may set a probe region 3 narrower than macular region.)
(The CPU 501 may set a probe region 3 narrower than standard macular region.)
(The CPU 501 may set a probe region 3 based on standard macular region.)
(The CPU 501 may set a probe region 3 broader than macular region.)
(The CPU 501 may set a probe region 3 broader than standard macular region.)

From a viewpoint of probing visual field characteristics mainly in macular region, if necessary, means for setting (confining) a probe region 3 locally based on (search, from a viewpoint of a predetermined resolution, of) whether a visual target (made of) such as character(s), symbol(s), etc. having a predetermined resolution can be resolved (recognized) in the visual field, may further be included.

The CPU 501 sets a plurality of probe points 4, with equal spacing, in the probe region 3, in accordance with a program for realizing the present invention of a macular region visual defect index calculation apparatus.
(A probe points setting means.)

The probe points 4 are set (defined) as positions on which a static visual target is sequentially displayed when probing visual field, and the CPU 501 does not display the probe points 4 explicitly in the visual field probe screen 1.

The CPU 501 displays the static visual target sequentially on the probe points 4 (for example, based on a response made by the subject, for example, via an input device (for example, a keyboard 303, a mouse 306, etc.) regarding visual perception of the static visual target) to probe the visual field corresponding to the probe points, in accordance with a program for realizing the present invention of a macular region visual defect index calculation apparatus.
(A visual target displaying and controlling means.)

The CPU 501 counts, and stores on a memory device (for example, a RAM 502, a HDD 504, etc.), a total number of the probe points 4 at which the static visual target has been displayed, in accordance with a program for realizing the present invention of a macular region visual defect index calculation apparatus.
(A first counting means.)

For example, in FIG. 4 which shows a preferred embodiment of the present invention, a total number, counted by the CPU 501, of the probe points 4 at which the static visual target has been displayed is the total number of the probe points 4 (within the probe region 3) in FIG. 4.

The CPU 501 detects that the static visual target being displayed has not been perceived by the subject, in accordance with a program for realizing the present invention of a macular region visual defect index calculation apparatus.
(A second detection means.)

Such a detection may be conducted via a second input device (for example, a left arrow key 303B, for example, in a keyboard 303) (for example, through a push of a left arrow key 303B, for example, in a keyboard 303 (in this case, that the static visual target has been visually perceived by the subject may be set to be detected, for example, via a right arrow key 303A)), for example, as a preferred embodiment, or such a detection may be conducted, for example, by setting a time limit.

The CPU 501 counts via an arithmetic unit and storing on a memory device (for example, a RAM 502, a HDD 504, etc.), the number of times of detecting that said static visual target has not been perceived by the subject, in accordance with a program for realizing the present invention of a macular region visual defect index calculation apparatus.
(A second counting means.)

For example, in FIG. 5 which shows a preferred embodiment of the present invention, the number of times, counted via an arithmetic unit by the CPU 501, of the CPU 501's detecting that said static visual target has not been perceived by the subject are (for example) the total number of the probe points shown in FIG. 5.
(i.e., The probe points shown in FIG. 5 reflect a scotoma located adjacent to the fixation image 201.)

The CPU 501, in accordance with a program for realizing the present invention of a macular region visual defect index calculation apparatus, calculates a visual defect index, via an arithmetic unit, by dividing said number of times counted and stored on the memory device (for example, a RAM 502, a HDD 504, etc.) by the CPU 501 (i.e., the number of times of the CPU 501's detecting that said static visual target has not been perceived by the subject (i.e., the value equivalent to (for example) the total number of the probe points shown in FIG. 5)), by said total number counted and stored on the memory device (for example, a RAM 502, a HDD 504, etc.) by the CPU 501 (i.e., a total number of the probe points 4 at which the static visual target has been displayed by the CPU 501 (i.e., the total number of the probe points 4 (within the probe region 3) in FIG. 4)).
(A visual defect index calculation means.)

Said visual defect index calculated via an arithmetic unit by the CPU 501, in accordance with a program for realizing the present invention of a macular region visual defect index calculation apparatus, is a visual defect index from a viewpoint of probing visual field characteristics mainly in macular region, that is, a macular region visual defect index 7.

FIG. 6 shows a preferred embodiment of the macular region visual defect index calculation and visual field mapping image generating aspect and display screen aspect of the present invention of a macular region visual defect index calculation apparatus.

In a visual field mapping screen 5 (a preferred embodiment of the present invention) which records the results of visual field probe on the visual field probe screen 1 using the static visual target, the results obtained from visual field probe toward the probe points 4 set (defined) in the probe region 3 on the visual field probe screen 1 are mapped (and visually reproduced) within a region in the visual field mapping screen corresponding to the probe region 6.
(a region in the visual field mapping screen corresponding to the probe region 6)

In a preferred embodiment of the present invention, for example, in visual field probe toward the probe points 4 set (defined) in the probe region 3 on the visual field probe screen 1, the CPU 501, in accordance with a program for realizing the present invention of a macular region visual defect index calculation apparatus, explicitly records with dark color (compared to a color with which the CPU 501 records the symbols representing that the visual target has been perceived, at the positions, corresponding to probe points positions in which that the visual target has been visually perceived is detected, in a region in the visual field mapping screen corresponding to the probe region 6) the symbols, which represent inability to visually perceive the visual target, at the positions, corresponding to the display positions (i.e., probe points positions) of the static visual target in which that the static visual target has not been visually perceived by the subject is detected, in a region in the visual field mapping screen corresponding to the probe region 6.

In a preferred embodiment of the present invention, for example, a scotoma located adjacent to the fixation image 201 is visually reproduced and explicitly mapped in the visual field mapping screen 5 as a group of the symbols image processed with the dark color.
(a scotoma located adjacent to the fixation image 201)

And in a preferred embodiment of the present invention, for example, a macular region visual defect index 7 calculated by the present invention of a macular region visual defect index calculation apparatus is shown in the visual field mapping screen 5.

What is claimed is:

1. A macular region visual defect index calculation apparatus comprising:
    means for generating, on an output device, a visual field probe screen for probing a visual field of a subject using a static visual target;
    means for displaying and controlling a fixation image to be fixated by the subject during a visual field probe, on the visual field probe screen generated by said visual field probe screen generating means;
    means for setting a circular region surrounding the fixation image displayed by said fixation image displaying and controlling means, as a probe region in order to probe the subject's visual field using the static visual target;
    means for setting a plurality of probe points, with equal spacing, in the probe region set by said probe region setting means;
    means for displaying and controlling the static visual target sequentially on the probe points set by said probe points setting means to probe the visual field corresponding to the probe points;
    first counting means for counting, and storing on a memory device, a total number of said probe points at which the static visual target has been displayed by said visual target displaying and controlling means;
    second detection means for detecting that the static visual target, displayed by said visual target displaying and controlling means, has not been perceived;
    second counting means for counting via an arithmetic unit and storing on a memory device, the number of times of detecting, through said second detection means, that said static visual target has not been visually perceived;
    and means for calculating a visual defect index, via an arithmetic unit, by dividing said number of times counted and stored on the memory device by said second counting means, by said total number counted and stored on the memory device by said first counting means;
    wherein said probe region being set locally from a viewpoint of probing visual field characteristics mainly in macular region, and said visual defect index being a visual defect index from a viewpoint of probing visual field characteristics mainly in macular region.

2. A program for causing a computer to realize the function comprising:
    means for generating, on an output device, a visual field probe screen for probing a visual field of a subject using a static visual target;
    means for displaying and controlling a fixation image to be fixated by the subject during a visual field probe, on the visual field probe screen generated by said visual field probe screen generating means;
    means for setting a circular region surrounding the fixation image displayed by said fixation image displaying and controlling means, as a probe region in order to probe the subject's visual field using the static visual target;

means for setting a plurality of probe points, with equal spacing, in the probe region set by said probe region setting means;

means for displaying and controlling the static visual target sequentially on the probe points set by said probe points setting means to probe the visual field corresponding to the probe points;

first counting means for counting, and storing on a memory device, a total number of said probe points at which the static visual target has been displayed by said visual target displaying and controlling means;

second detection means for detecting that the static visual target, displayed by said visual target displaying and controlling means, has not been perceived;

second counting means for counting via an arithmetic unit and storing on a memory device, the number of times of detecting, through said second detection means, that said static visual target has not been visually perceived;

and means for calculating a visual defect index, via an arithmetic unit, by dividing said number of times counted and stored on the memory device by said second counting means, by said total number counted and stored on the memory device by said first counting means;

wherein said probe region being set locally from a viewpoint of probing visual field characteristics mainly in macular region, and said visual defect index being a visual defect index from a viewpoint of probing visual field characteristics mainly in macular region.

3. An operational method for a macular region visual defect index calculation apparatus comprising:

a step of means for generating, on an output device, a visual field probe screen for probing a visual field of a subject using a static visual target;

a step of means for displaying and controlling a fixation image to be fixated by the subject during a visual field probe, on the visual field probe screen generated by said step of visual field probe screen generating means;

a step of means for setting a circular region surrounding the fixation image displayed by said step of fixation image displaying and controlling means, as a probe region in order to probe the subject's visual field using the static visual target;

a step of means for setting a plurality of probe points, with equal spacing, in the probe region set by said step of probe region setting means;

a step of means for displaying and controlling the static visual target sequentially on the probe points set by said step of probe points setting means to probe the visual field corresponding to the probe points;

a step of first counting means for counting, and storing on a memory device, a total number of said probe points at which the static visual target has been displayed by said step of visual target displaying and controlling means;

a step of second detection means for detecting that the static visual target, displayed by said step of visual target displaying and controlling means, has not been perceived;

a step of second counting means for counting via an arithmetic unit and storing on a memory device, the number of times of detecting, through said step of second detection means, that said static visual target has not been visually perceived;

and a step of means for calculating a visual defect index, via an arithmetic unit, by dividing said number of times counted and stored on the memory device by said step of second counting means, by said total number counted and stored on the memory device by said step of first counting means;

wherein said probe region being set locally from a viewpoint of probing visual field characteristics mainly in macular region, and said visual defect index being a visual defect index from a viewpoint of probing visual field characteristics mainly in macular region.

4. A non-transitory computer-readable recorded medium recording a program for causing a computer to realize the function comprising:

means for generating, on an output device, a visual field probe screen for probing a visual field of a subject using a static visual target;

means for displaying and controlling a fixation image to be fixated by the subject during a visual field probe, on the visual field probe screen generated by said visual field probe screen generating means;

means for setting a circular region surrounding the fixation image displayed by said fixation image displaying and controlling means, as a probe region in order to probe the subject's visual field using the static visual target;

means for setting a plurality of probe points, with equal spacing, in the probe region set by said probe region setting means;

means for displaying and controlling the static visual target sequentially on the probe points set by said probe points setting means to probe the visual field corresponding to the probe points;

first counting means for counting, and storing on a memory device, a total number of said probe points at which the static visual target has been displayed by said visual target displaying and controlling means;

second detection means for detecting that the static visual target, displayed by said visual target displaying and controlling means, has not been perceived;

second counting means for counting via an arithmetic unit and storing on a memory device, the number of times of detecting, through said second detection means, that said static visual target has not been visually perceived;

and means for calculating a visual defect index, via an arithmetic unit, by dividing said number of times counted and stored on the memory device by said second counting means, by said total number counted and stored on the memory device by said first counting means;

wherein said probe region being set locally from a viewpoint of probing visual field characteristics mainly in macular region, and said visual defect index being a visual defect index from a viewpoint of probing visual field characteristics mainly in macular region.

* * * * *